(12) United States Patent
Salnik et al.

(10) Patent No.: US 7,248,367 B2
(45) Date of Patent: Jul. 24, 2007

(54) CHARACTERIZATION OF ULTRA SHALLOW JUNCTIONS IN SEMICONDUCTOR WAFERS

(75) Inventors: Alex Salnik, Castro Valley, CA (US); Lena Nicolaides, Castro Valley, CA (US); Jon Opsal, Livermore, CA (US)

(73) Assignee: Therma-Wave, Inc., Fremont, CA (US)

( * ) Notice: Subject to any disclaimer, the term of this patent is extended or adjusted under 35 U.S.C. 154(b) by 385 days.

(21) Appl. No.: 10/796,603

(22) Filed: Mar. 8, 2004

(65) Prior Publication Data

US 2004/0251927 A1 Dec. 16, 2004

Related U.S. Application Data

(60) Provisional application No. 60/477,255, filed on Jun. 10, 2003, provisional application No. 60/496,117, filed on Aug. 19, 2003.

(51) Int. Cl.
*G01N 21/00* (2006.01)
(52) U.S. Cl. ..................................... 356/432
(58) Field of Classification Search ............... 356/432, 356/445
See application file for complete search history.

(56) References Cited

U.S. PATENT DOCUMENTS

| | | | |
|---|---|---|---|
| 4,579,463 A | 4/1986 | Rosencwaig et al. | 374/57 |
| 4,634,290 A | 1/1987 | Rosencwaig et al. | 374/5 |
| 4,636,088 A | 1/1987 | Rosencwaig et al. | 374/5 |
| 5,978,074 A | 11/1999 | Opsal et al. | 356/72 |
| 6,049,220 A | 4/2000 | Borden et al. | 324/765 |
| 6,323,951 B1 | 11/2001 | Borden et al. | 356/502 |
| 6,658,037 B2 * | 12/2003 | Kahen et al. | 372/70 |
| 6,870,868 B2 * | 3/2005 | Kahen et al. | 372/39 |
| 6,888,632 B2 * | 5/2005 | Smith | 356/369 |
| 2002/0167326 A1 | 11/2002 | Borden et al. | 327/752 |

OTHER PUBLICATIONS

J. Opsal et al., "Theory of the Temporal Behavior of Modulated Optical Reflectance in Silicon," *Digest of 5th International Topical Meeting of Photoacoustic and Photothermal Phenomena* (Heidelberg, Germany), Jul. 27-30, 1987, pp. coversheet, 103-104.
J. Opsal et al., "Temporal behavior of modulated optical reflectance in silicon," *J. Appl. Phys.*, vol. 61, No. 1, Jan. 1, 1987, pp. 240-248.
A. Rosencwaig et al., "Temporal Behavior of Modulated Reflectance Signal in Silicon," from Review of Progress in Quantitative Nondestructive Evaluation, *Rev. Progress in QNDE*, vol. 6A (1987), pp. 237-244.
A. Rosencwaig et al., "Temporal Behavior of Modulated Optical Reflectance in Silicon," Abstract submitted for the Mar. 1986 Meeting of the American Physical Society Mar. 31-Apr. 4, 1986, *Bulletin of the American Physical Society* 31(3), Mar. 1986, p. 633.
Excerpt: Therma-Probe 420 User Manual; Theory of Operation; Damage Relaxation (Decay Factor), 1 page in length. [See p. 3 of this Information Disclosure Statement for explanation].
In re U.S. Appl. No. 10/387,259, filed Mar. 12, 2003, entitled "Ion Implant Monitoring Through Measurement of Modulated Optical Response," by Alex Salnik et al., 17 pages in length.

* cited by examiner

*Primary Examiner*—Layla G. Lauchman
*Assistant Examiner*—Michael A. Lyons
(74) *Attorney, Agent, or Firm*—Stallman & Pollock LLP

(57) ABSTRACT

To measure USJ profile abruptness, a PMR-type optical metrology tool is to perform a series of two or more measurements, each with different pump/probe beam separations. Quadrature (Q) and in-phase (I) measurements are obtained for each measurement and used to derive a line in I-Q space. An abruptness measurement is derived by comparing the line slope to a similar line slope obtained for a sample having a known USJ profile. USJ profile depth is measured by obtaining quadrature (Q) values for one or more measurements. Each Q value is translated to a corresponding depth measurement using a table or similar lookup device.

16 Claims, 9 Drawing Sheets

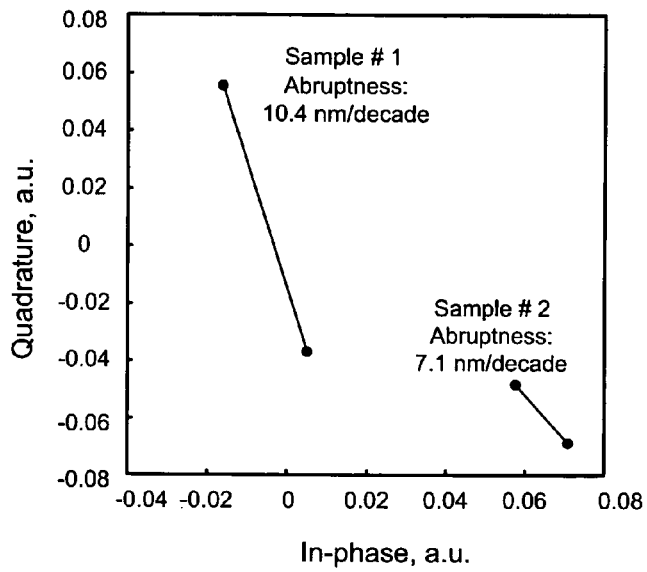
Fig. 6
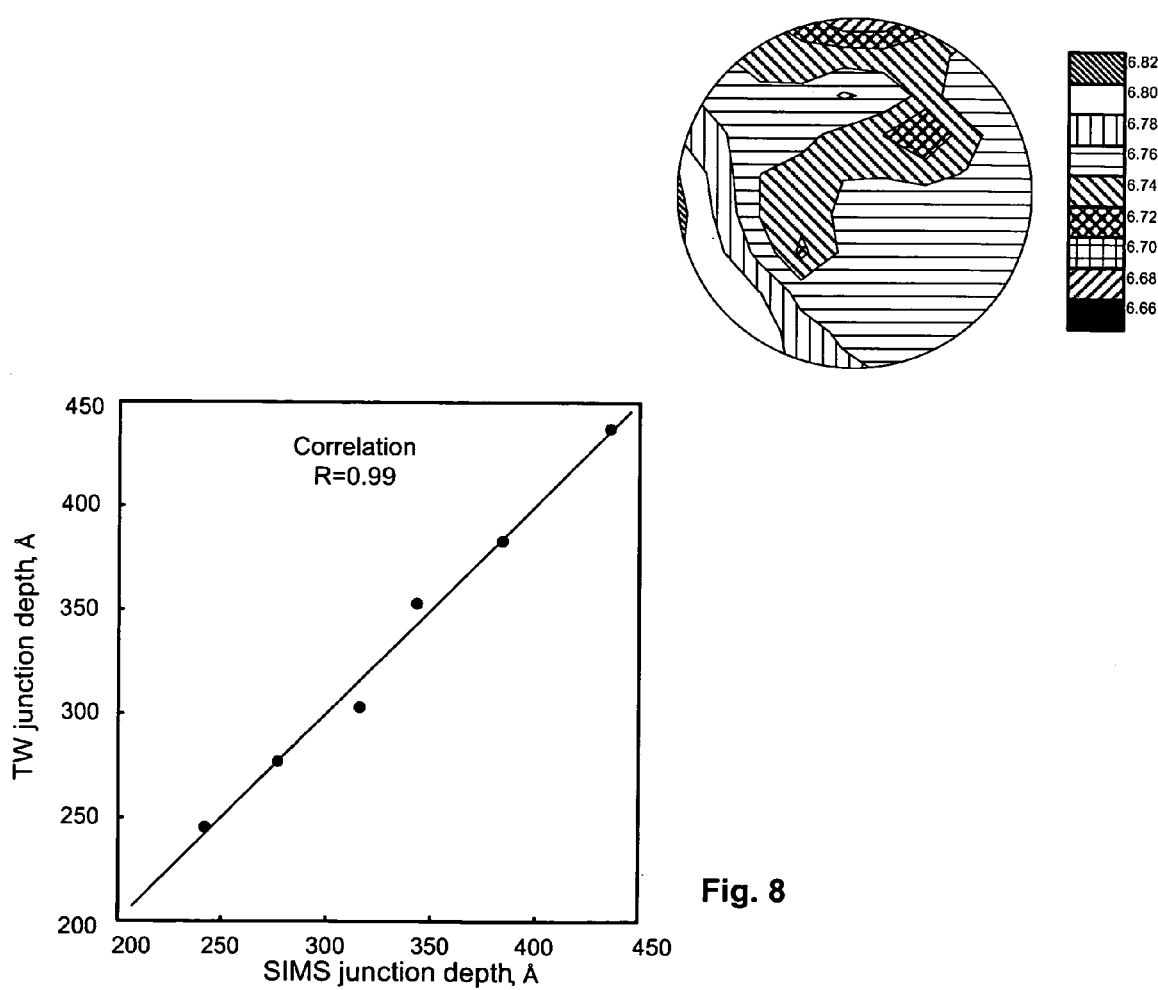
Fig. 7
Fig. 8

Sample #1,
depth

Sample #2,
depth

Sample #3,
depth

Sample #4,
depth

Sample #5,
depth

Sample #6,
depth

Sample #1, TW$_0$

Sample #1, TW$_{10}$

Sample #2, TW$_0$

Sample #2, TW$_{10}$

Sample #3, TW$_0$

Sample #3, TW$_{10}$

Sample #1, DF

Sample #2, DF

Sample #3, DF

Sample #3,
depth

Sample #3,
abuptness

Sample #3,
DF

CHARACTERIZATION OF ULTRA SHALLOW JUNCTIONS IN SEMICONDUCTOR WAFERS

PRIORITY CLAIM

The present application claims priority to U.S. Provisional Patent Application Ser. No. 60/477,255, filed Jun. 10, 2003, and U.S. Provisional Patent Application Ser. No. 60/496,117, filed Aug. 19, 2003, the disclosures of which are incorporated in this document by reference.

TECHNICAL FIELD

The subject invention relates to optical devices used to non-destructively evaluate semiconductor wafers. In particular, the present invention relates to methods for characterizing ultra shallow junctions in semiconductors.

BACKGROUND OF THE INVENTION

As semiconductor geometries continue to shrink, manufacturers have increasingly turned to optical techniques to perform non-destructive inspection and analysis of semiconductor wafers. Optical techniques typically apply an incident beam (often referred to as a probe beam) to a sample and then detect and analyze the reflected energy. This type of inspection and analysis is known as optical metrology and is performed using a range of different optical techniques.

One widely used type of optical metrology is known as photo modulated reflectance or PMR. As shown in FIG. 1A, a typical PMR-type system includes a pump laser and a probe laser. The pump laser intensity is varied to create an intensity-modulated pump beam. The pump beam is projected against the surface of a sample and absorbed causing localized excitation of the sample. As the pump laser is modulated, the localized excitation (and subsequent relaxation) creates a train of thermal and plasma waves within the sample. These waves reflect and scatter off various features and interact with various regions within the sample in a way that alters the flow of heat and/or plasma from the pump beam spot.

The presence of the thermal and plasma waves has a direct effect on the surface reflectivity of the sample. Features and regions below the sample surface that alter the passage of the thermal and plasma waves will therefore alter the optical reflective patterns at the surface of the sample. By monitoring the changes in reflectivity of the sample at the surface, information about characteristics below the surface can be obtained.

To monitor the surface changes, a probe laser is used to direct a probe beam at a portion of the sample that is excited by the pump laser. The sample reflects the probe beam and a photodetector records the intensity of the reflected probe beam. The output signal from the photodetector is filtered to isolate the changes that are synchronous with the pump beam modulation. For most implementations, this is performed using a heterodyne or lock-in detector (See U.S. Pat. No. 5,978,074 and in particular FIG. 2 there for a discussion of such a lock-in amplifier/detector). Devices of this type typically generate separate "in-phase" (I) and "quadrature" (Q) outputs. These outputs are then used to calculate amplitude and phase of the modulated signal using the following equations:

$$Amplitude = \sqrt{I^2 + Q^2} \quad (1)$$

$$Phase = \arctan(Q/I) \quad (2)$$

The amplitude and phase values are used to deduce physical characteristics of the sample. In most cases, this is done by measuring amplitude values (amplitude is used more commonly than phase) for one or more specially prepared calibration samples, each of which has known physical characteristics. The empirically derived values are used to associate known physical characteristics with corresponding amplitude values. Amplitude values obtained for test samples can then be analyzed by comparison to the amplitude values obtained for the calibration samples.

Characterization of samples using I and Q outputs is described in U.S. patent application Ser. No. 10/387,259, filed Mar. 12, 2003, assigned to the same assignee and incorporated here by reference. In this case, experimentally obtained in-phase and quadrature signals are plotted in I-Q coordinates, analyzed, and compared to calibration data.

The PMR-type system shown in FIG. 1A includes a beam scanner for shifting the X-Y position of the pump beam on the sample surface. This allows the pump beam to be accurately located to coincide with the portion of the sample illuminated by the probe beam. As shown in FIG. 1B, the beam scanner can also be used to separate the pump and probe v beams on the sample surface. As described in U.S. Pat. No. 5,978,074 (incorporated here by reference), this mechanism can be used to scan the separation between pump and probe beams. Amplitude and phase (or I and Q) are measured and analyzed as a function of pump-probe beam separation.

As part of the manufacturing process, ions (or dopants) are added to the near-surface region of semiconductors using a process known as implantation. The implanted region (with its relatively high dopant concentration) overlays a non-implanted region where dopant concentrations are relatively low. The transition between the implanted region and the non-implanted region is commonly referred to as a junction. For advanced semiconductor manufacturing, it is generally desirable for the implanted region to be shallow, typically 500 Å or less. Devices of this type are generally referred to as having ultra-shallow junctions or USJ.

The quality of USJ wafers (and the processes used to create USJ wafers) is typically assessed using two parameters: junction depth and junction abruptness. Junction depth (Xj) is the depth at which the junction between the implanted and non-implanted regions is located. Abruptness (measured in nm/dec) characterizes how quickly the junction transitions between high level and low level dopant concentrations. To illustrate, FIG. 2, shows several USJ profiles obtained by using the Secondary Ion Mass Spectroscopy (SIMS) technique having different junction depths and abruptness (the lower the abruptness value in nm/decade the more abrupt is the profile).

In practice, shallow junction depth is typically accomplished by implantation at high dopant dose and low energy. Abruptness is typically achieved using a rapid thermal annealing (RTA) process. In practice, the required junction depth is often relatively easy to achieve. However, keeping the USJ profile abrupt and close to the surface after anneal is a big challenge. As a result, techniques to measure junction depth and abruptness are critical for the manufacture of USJ semiconductors.

Incompleteness of anneal is another parameter that is crucial to USJ characterization. Incompleteness appears when non-uniformities in structural damage caused by ion implantation along with malfunctioning of the RTA process and other types of annealing processes result in residual structural damage areas on the surface of a semiconductor wafer after anneal. This incomplete anneal should also be monitored to increase manufacturing yield and to ensure high performance characteristics of a semiconductor device.

A number of techniques have been developed to characterize the effectiveness of USJ processes. Destructive and contact techniques include secondary ion mass spectroscopy (SIMS), transmission electron microscopy (TEM), and spreading resistance depth profiling (SRP). These methods are capable of providing detailed USJ profile information, but at the expense of a turnaround time that is usually measured in days or even weeks or at the expense of damaging the surface with contacts. Alternately, U.S. patent application Ser. No. 09/799,481 (published as U.S. 2002/0167326) describes a non-destructive method for measuring profile abruptness. According to this method, several amplitude measurements are taken at different powers of the pump laser in a photothermal system similar to that described above. The resulting power dependencies are than fitted to a function (power series) and the second (quadratic) coefficient of that function is correlated to profile abruptness. FIG. 3 shows the resulting calibration dependence relating quadratic coefficient and USJ profile abruptness measured independently using another destructive technique. This method has several disadvantages. First, increasing pump power (up to 100 mW) could result in altering of semiconductor device properties. Secondly, interpretation of experimental results in this method is compromised by strong signal non-linearity arising as a result of excitation with high pump power densities. Finally, this method is time-consuming because of the fitting involved and is not sensitive enough to ensure its reliable performance.

SUMMARY OF THE INVENTION

The present invention offers a series of methods for characterizing USJ profiles including methods for characterizing depth, abruptness, and anneal incompleteness. To measure USJ profile abruptness, a PMR-type optical metrology tool is used to perform a series of two or more measurements. The separation between the pump and probe beams is changed for each successive measurement. Typically, this means that measurements are obtained, for example, at zero (coincident pump and probe beams) and one µm beam separation. At each separation, quadrature (Q) and in-phase (I) measurements are obtained.

A line is then fitted to the measurements in the I-Q plane. The slope of that line corresponds to the abruptness of the sample being analyzed. To determine the exact correspondence, a calibration phase is typically used where a similar slope is obtained for a sample having a known USJ profile. Abruptness can then be computed by comparing the slope associated with the known sample to slope information obtained for samples under test.

For a second implementation of the abruptness measuring method, the pump and probe beams are maintained a fixed separation. The power density provided by the pump beam is altered for each successive measurement. I and Q values are obtained for each measurement and used to derive a corresponding slope in I-Q space. The slope is compared to a similar slope associated with a known USJ profile to determine abruptness.

To measure USJ profile depth, a PMR-type optical metrology tool is used to perform a series of one or more measurements. Quadrature (Q) measurements are obtained for each measurement and are linearly scaled (typical using a table or other lookup mechanism) to derive USJ profile depth values.

To measure anneal incompleteness, a PMR-type optical metrology tool is developed which provides a "decay factor" stationary mapping. Each measurement is performed stationary along the wafer. During each measurement, the reflected probe beam intensity is monitored and recorded as a function of time. Changes in the measured probe beam over time characterize the anneal performance. The "decay factor" at each measurement is calculated as the ratio of the signal from an initial point (typically when the pump beam is initially focused on the sample under test) to the signal at some subsequent point (typically a defined interval such as ten seconds). The decay factor is typically defined to be close to unity when the sample tested is completely annealed. For wafers having residual damage, the decay factor will be greater or less than unity. A complete map of the annealing behavior of the wafer can be provided in terms of "decay factor" values.

The methods described above are intended to be used separately or in combination. They may be used to perform single inspections of multiple measurements within the same sample. Multiple measurements are especially useful to map a parameter (decay factor, USJ depth or USJ profile) for all or a portion of a sample. Multiple measurements may also be used to derive average and standard deviation values for any of the three parameters.

BRIEF DESCRIPTION OF THE DRAWINGS

FIG. 6 shows modulated reflectivity measurements values obtained at varying pump power density mapped in the I-Q plane for two samples.

FIG. 7 shows a map of a sample wafer showing USJ profile abruptness measurements obtained by a method of the present invention.

FIG. 8 shows the correlation between USJ profile depth measurements obtained using a method provided by the present invention and independently obtained SIMS profiles.

DETAILED DESCRIPTION OF THE PREFERRED EMBODIMENTS

The present invention includes a series of methods for characterizing USJ profiles. As will be described in the following sections, this includes methods for characterizing USJ abruptness, USJ depth and anneal incompleteness.

USJ Abruptness Variable Beam Separation Method

Figure 1A:
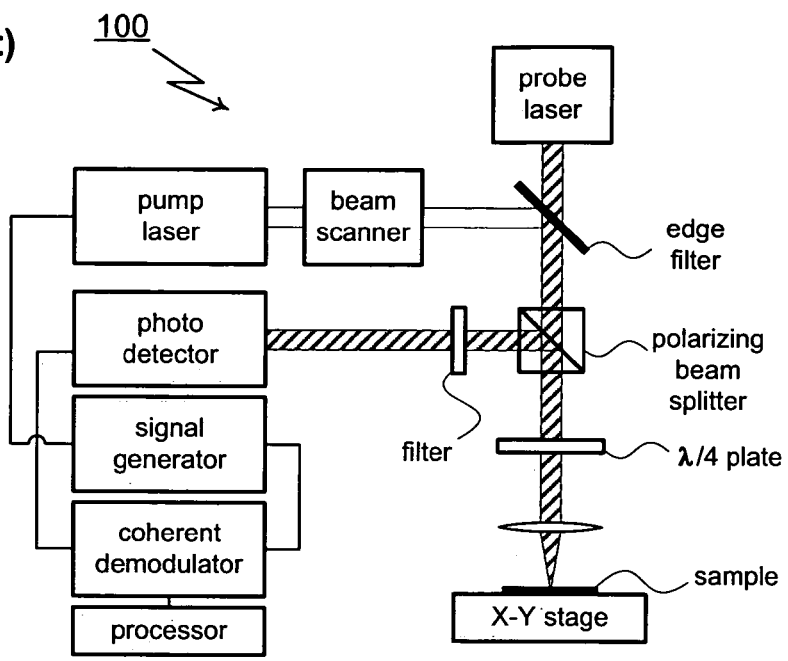
FIGS. 1A and 1B show prior art optical metrology systems.
Figure 1B:
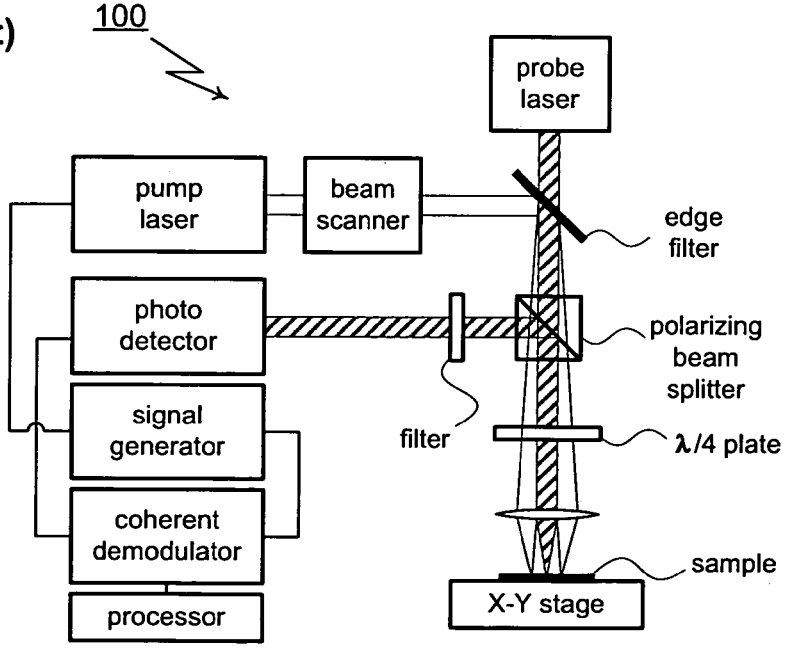

To measure profile abruptness, a PMR system of the type generally shown in FIG. 1B is used. During inspection, a series of two or more measurements are made. For each successive measurement, the beam scanner component of the PMR system is used to change the separation between the pump and probe beams producing a range of separations between zero (coincident pump and probe beams) and one µm. At each separation, I and Q measurements are obtained.

Figure 4:
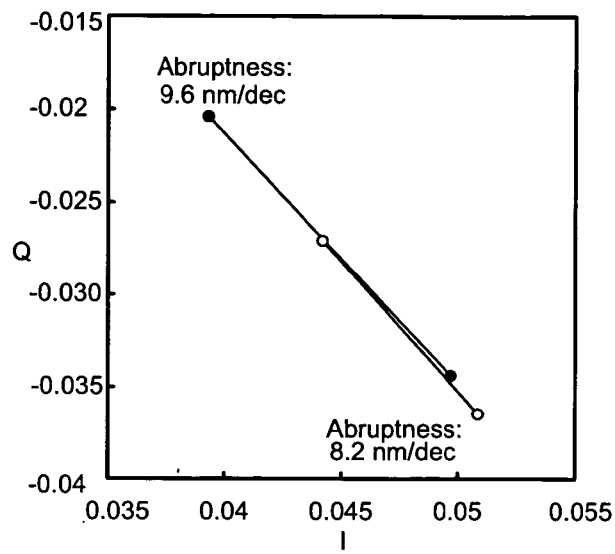
FIG. 4 shows modulated reflectivity measurements values obtained at varying pump/probe beam offsets mapped in the I-Q plane for two samples.

The measurements obtained at the different separations are analyzed in I-Q space. To illustrate, FIG. 4 shows measurements obtained for two samples (with one series being shown in black circles and the other shown in white circles). A line is plotted to each measurement. The slope of this line is related to abruptness of the USJ profile of the sample being inspected. In this case, the white series of measurements has a steeper slope and greater abruptness (8.2 nm compared to 9.6 nm per decade).

It should be noted that the slope information is not a direct measurement of abruptness—the values of 8.2 nm and 9.6 nm per decade shown in FIG. 4 are not deduced directly from the slopes of the two measurement series. For this reason, the measurement process is typically subdivided into two phases: a calibration phase and a measurement phase. During the calibration phase, a sample is measured using the procedure just described to obtain the slope information as shown in FIG. 4. The USJ profile of the sample is then obtained using a second testing method. The second method is typically destructive, but may be any suitable technique. The second measurement provides a numerical value that describes the abruptness of the calibration sample.

In the measurement phase, one or more samples are measured using the PMR system to obtain the slope information as shown in FIG. 4. The slope information for each sample is used, along with the slope information and abruptness information obtained during the calibration phase to compute an abruptness value for each sample. In other words, the abruptness of each sample is computed as a function of three values: 1) the slope information obtained for the sample using the PMR system at a series of different pump/probe beam offsets, 2) the slope information obtained during the calibration phase, and 3) the independently measured abruptness information obtained during the calibration phase.

Figure 5:
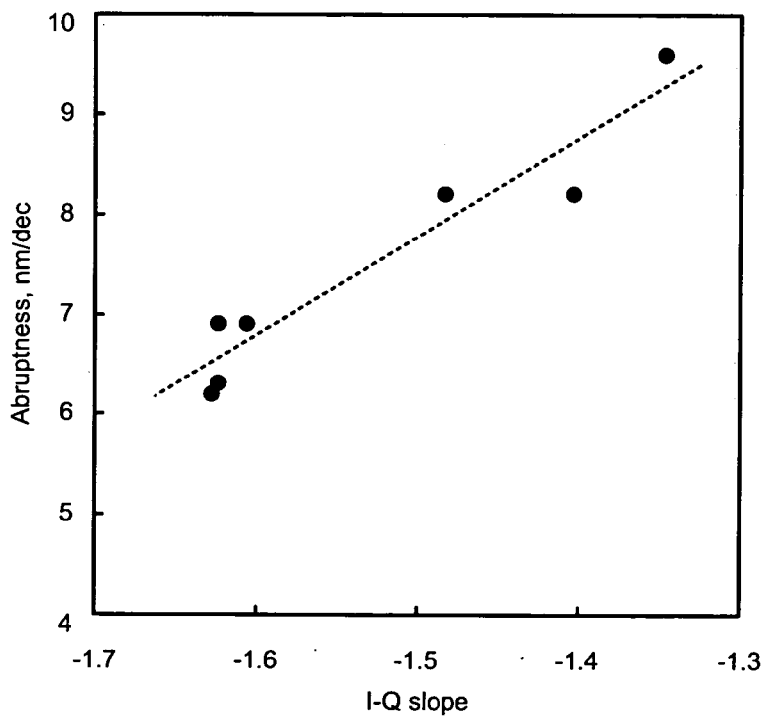
FIG. 5 shows the correlation between I-Q slope values obtained at varying pump/probe beam offsets and independently obtained SIMS profiles.

FIG. 5 compares slope information obtained using the method just described to independent USJ profile abruptness measurements. As may be appreciated, there is substantial correlation between the I-Q slope values and the independent measurements.

USJ Abruptness, Variable Power Density Method

Instead of varying pump and probe beam separation, another approach is to vary pump beam power density. The present invention provides a second method for measuring profile abruptness that uses this approach. In the case of the second method, I and Q measurements are taken on a sample at two or more pump beam power densities. In a preferred embodiment pump power density is changed (decreased) by inserting a neutral filter into the optical path of the pump beam. In an alternative embodiment, the pump power density is changed by changing the pump beam spot size. As before, the resulting I and Q measurements are plotted in I-Q space. A line is then fitted to the measurements and the slope of the line is extracted and correlated to USJ profile abruptness measured independently using another (typically destructive) technique. This correlation is used to determine abruptness on other wafers with unknown parameters. FIG. 6 shows measurements obtained for two samples (with one series being shown in black circles and the other shown in white circles) obtained using the variable power density method. As for the first method, a strong correlation is seen between the slope in I-Q plane and profile abruptness (note different scales in FIGS. 4 and 6).

Figure 2:
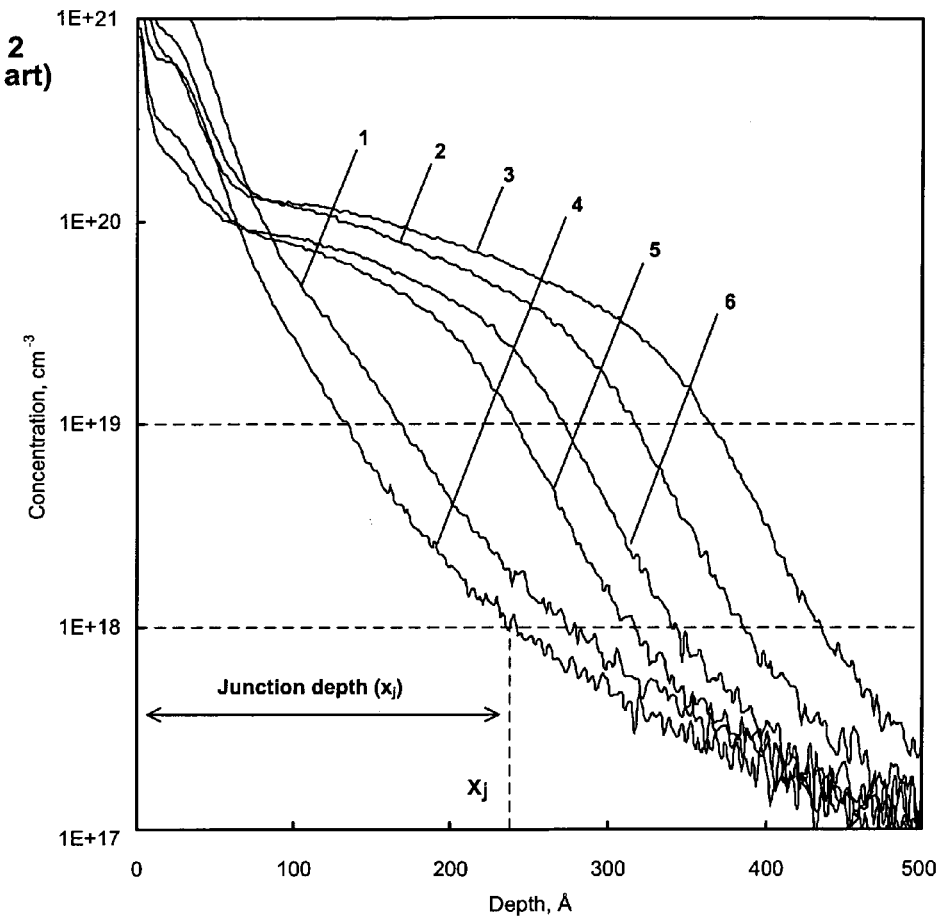
FIG. 2 show secondary ion mass spectroscopy (SIMS) concentration profiles obtained for six samples having different USJ depths and abruptnesses.
Figure 3:
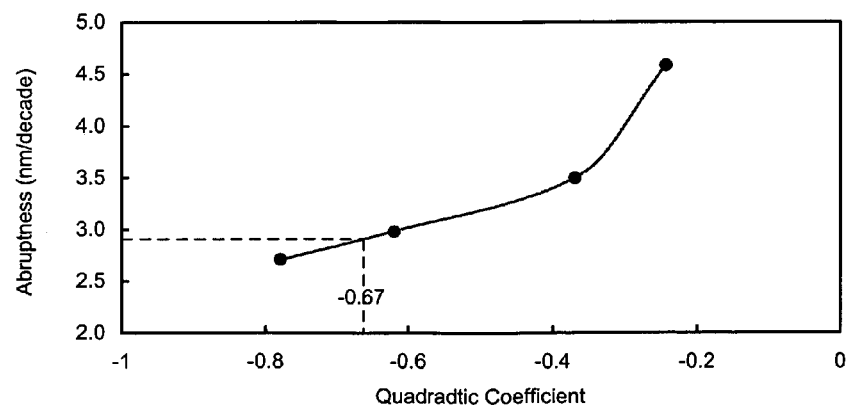
FIG. 3 shows a prior art method of correlating photo modulated reflectivity measurements to USJ profile abruptness.

It should be noted that, despite of their similarity in using I-Q space, the two methods described above are based on quite different physical assumptions and experimental geometries. These methods might have different sensitivities to a variety of junction properties, other than profile abruptness (dopant nature and concentration, inhomogeneities, etc.). It might be advantageous to use both methods in combination to obtain more reliable abruptness data. In addition, USJ profiles can have different abruptness at different concentration levels. For example, in FIG. 2 profile #4 has a clearly visible change in abruptness as the ion concentrations decreases below the $10^{18}$ $cm^{-3}$ level. Complementary use of both methods could potentially provide more information about profiles exhibiting nonmonotonic behavior with changing abruptness.

An important feature of both measurement methods (power density and pump-probe beam separation) is the ability to obtain measurements rapidly. In fact, it is entirely practical to make multiple abruptness measurements at different locations within the sample under test even in production environments. FIG. 7 shows an abruptness map constructed by measuring twenty-one locations within a sample wafer. As is clearly shown, abruptness varies over the sample surface. In this way, both measurement methods may be used to scan a wafer to assess abruptness uniformity. Alternately, multiple measurements may be averaged or otherwise combined to characterize the abruptness of the USJ profile.

It should be understood that the methods of the present invention is not limited to the combination of I and Q values obtained directly from the experiment, and may use any combination of these parameters that is beneficial.

USJ Depth, PMR Q Data Method

To measure USJ depth, a PMR system of the type generally shown in FIG. 1(a) is used. During inspection, Q data is obtained for one or more locations on the sample under test. Typically, this is performed with no separation between the pump and probe beams. Q data is preferred because the Q-component of the total PMR signal for post anneal USJ samples is driven primarily by plasma wave related effects. PMR amplitude, on the other hand is more sensitive to damage-related phenomena. In fully annealed USJ wafers, the plasma wave is quite sensitive to physical non-uniformities such as the boundary between the highly doped USJ region and the relatively low-doped substrate. This makes the Q component sensitive to USJ profile depth and therefore may provide a potentially more accurate measure of USJ depth when compared to the more conventional PMR amplitude measurement.

The Q data obtained from each sample is used to derive corresponding USJ depth measurements. Typically, this is done using a correlation table that maps Q data to USJ depth.

Other implementations may use other methods to correlate Q data to depth measurements.

FIG. 8 compares a series of USJ depth measurements obtained by using the method just described to independently obtained USJ depth measurements. As may be appreciated, the correlation between the results of the two methods is excellent (correlation coefficient R=0.99) for USJ depths ranging from >250 Å to <500 Å. This high degree of correlation is particularly remarkable because the Q-based measurements represent USJ depths averaged across the entire wafer surface while an independent SIMS analysis was performed only at a single central point on each wafer.

Figure 9:
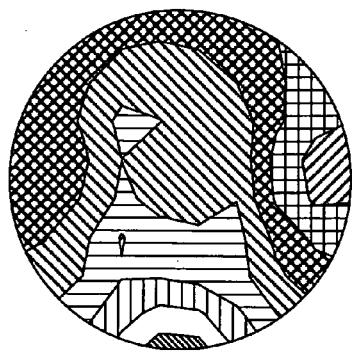
FIG. 9 shows respective maps for six sample wafers showing USJ profile depth measurements obtained by a method provided the present invention.
Figure 9:
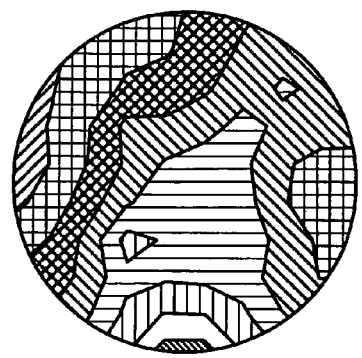
Figure 9:
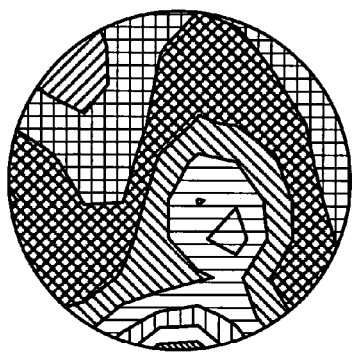
Figure 9:
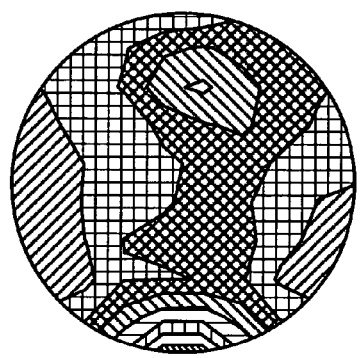
Figure 9:
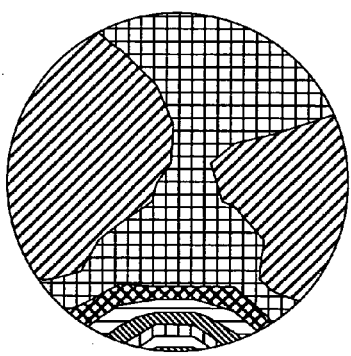
Figure 9:
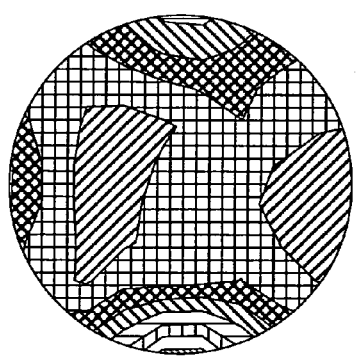

FIG. 9 shows two-dimensional 21-point maps of USJ depths obtained by scanning the wafer surface (note, different depth scale for each sample at the right). The relative speed of the measurement method allows the maps shown in FIG. 9 to be rapidly constructed, even in production environments. Multiple measurements may also be used in non-graphical ways to characterize entire samples or sample portions. For example, multiple measurements may be combined to compute average and standard deviations for USJ depth within a sample under test.

As shown in FIG. 9, USJ depths vary significantly across the surface of each wafer. It has been found that precision in USJ depth measurements is better than 1.5%, much less than the difference in junction depth observed in the area maps in FIG. 9. Wafer number five has the most homogeneous USJ depth distribution among all wafers studied: more than 80% of its surface has junction depth variations of less than 5 Å. A radial pattern (wafer number three) and band-like patterns (wafers two and four) indicative of nonuniform RTA heating are clearly visible in FIG. 9. Nonuniformity of junction depth across the wafer surface observed in FIG. 9 can be caused by small variations (few degrees) in anneal temperature and/or by the local effects and could have a significant impact on the production yield.

As can be clearly seen in FIG. 9, all scans exhibit maximum junction depths located close to the bottom of the wafer. This phenomenon (also called "hot spot") indicates possible problems with spatial temperature uniformity during the RTA and could have been missed by any single-point analysis.

To conclude this section, it is noted that the depth measurement method provided by the present invention allows for precise measuring of an average USJ junction depth and high-resolution depth distribution mapping across the surface of the wafer in a short time, thus comparing favorably with time-consuming and destructive single-point SIMS analysis.

Characterization of Anneal

Figure 10:
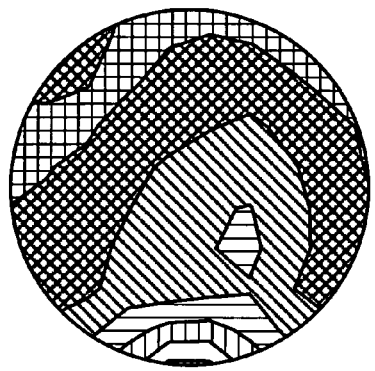
FIG. 10 shows PMR maps for three sample wafers. Each wafer is shown before and after a simulated annealing process, $TW_0$ is stands for the initial thermal wave signal (zero time) while $TW_{10}$ is the thermal wave signal after 10 sec.
Figure 10:
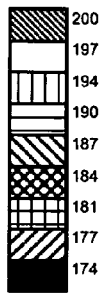
Figure 10:
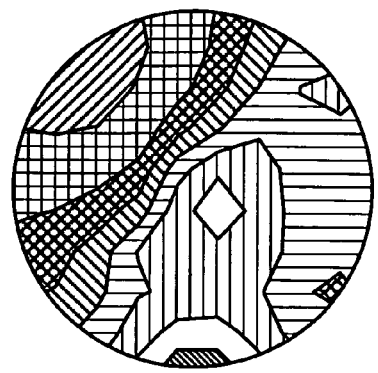
Figure 10:
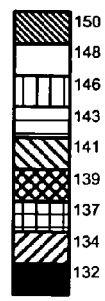
Figure 10:
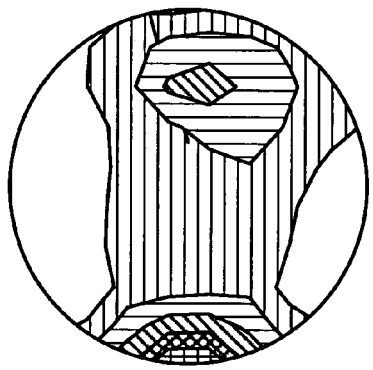
Figure 10:
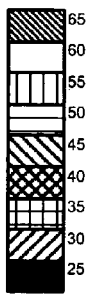
Figure 10:
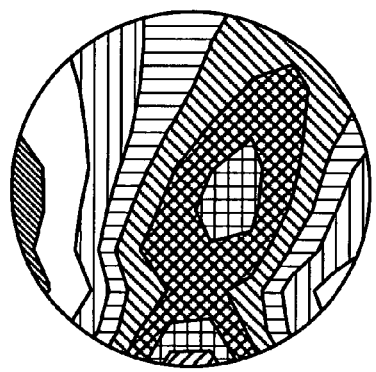
Figure 10:
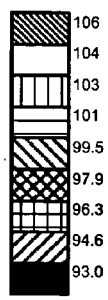
Figure 10:
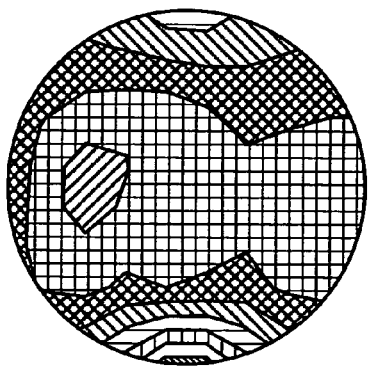
Figure 10:
Figure 10:
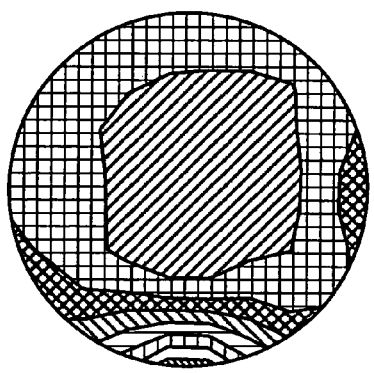
Figure 10:
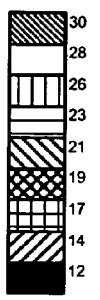

To measure anneal incompleteness and/or surface electronic states, a PMR system of the type generally shown in FIG. 1(a) is used. During inspection, the reflected probe beam (the TW signal) is monitored and recorded as a function of time. In samples that have these features, the signal changes over time. FIG. 10 illustrates this effect for a series of three sample wafers. For each wafer, a map is shown of the TW signal taken at the beginning of the measurement process (that signal is referred to as the $TW_0$ signal). A second map of each wafer shows the TW signal recorded after ten seconds of exposure to the pump beam (that signal is referred to as the $TW_{10}$ signal). As is clearly shown, in wafers having residual damage and/or surface states, there is significant difference between the $TW_0$ and $TW_{10}$ signals.

Figure 11:
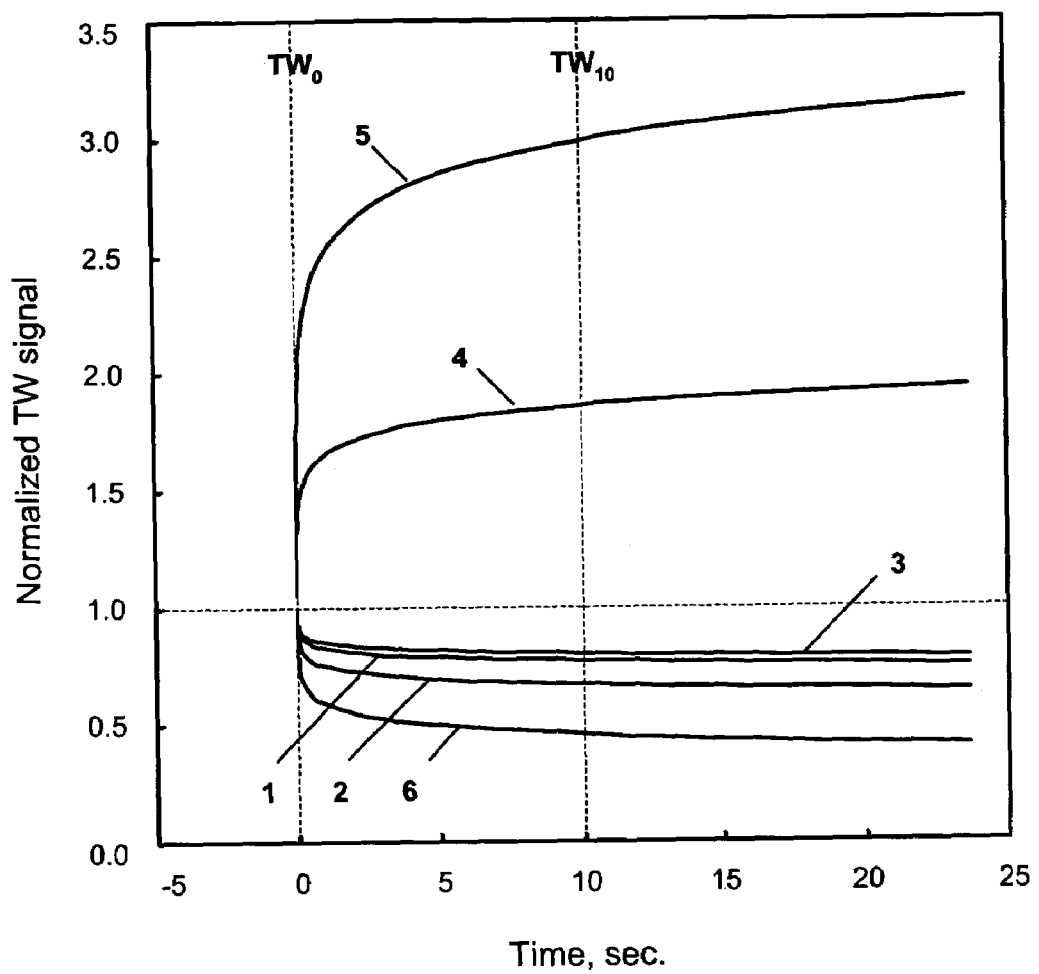
FIG. 11 shows PMR signals for six sample wafers plotted against time during a simulated annealing process.

The recorded TW signal is used to develop a curve which is then fitted to an exponential decay. FIG. 11 shows curves of this type for six different sample wafers. A decay factor characterizing the anneal completeness is then calculated using the relation:

$$DF = \frac{TW_{10}}{TW_0}$$

Figure 12:
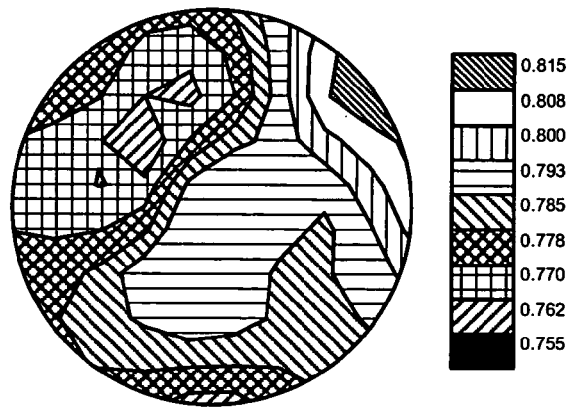
FIG. 12 shows decay factor (DF) maps for the three wafers of FIG. 10.
Figure 12:
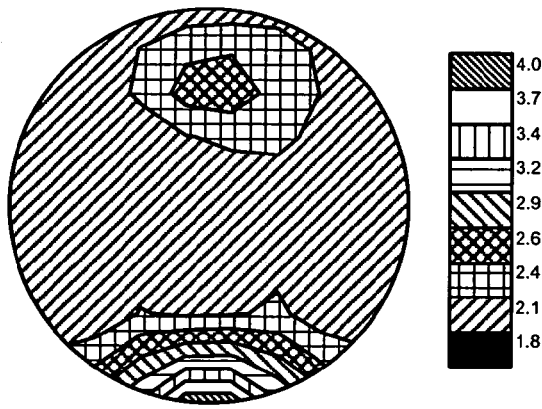
Figure 12:
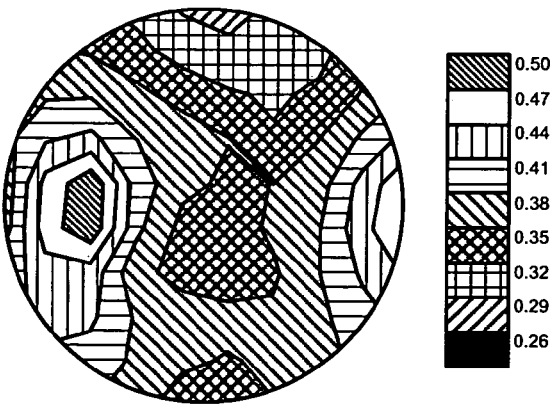

The DF parameter characterizes completeness of the anneal process and/or the presence of surface states at the location where it is recorded. The closer DF is to unity, the better is the quality of the annealing process. FIG. 12 maps the calculated DF parameter for the three sample wafers originally shown in FIG. 10. As previously described for other methods, the DF parameter may be measured at a single location or at multiple sample locations allowing the computation of average, standard deviation and other values.

Figure 13:
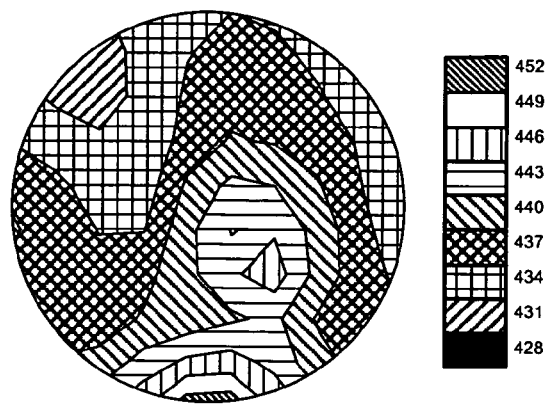
FIG. 13 shows USJ profile abruptness maps, USJ depth maps and decay factor maps for the third wafer of FIG. 10.
Figure 13:
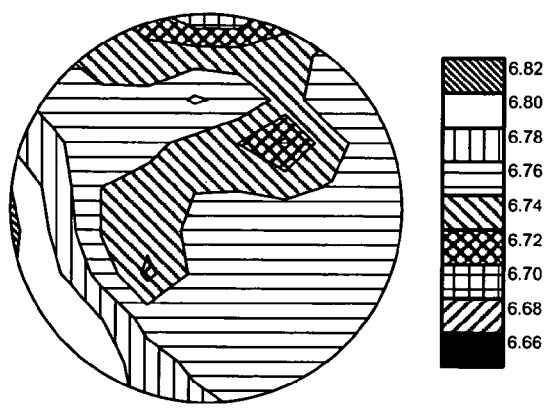
Figure 13:
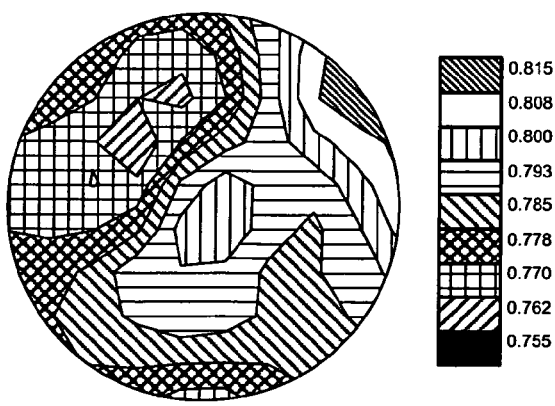

It should also be noted that the measurement methods of the present invention may be used separately to measure any of the described parameters. The methods may also be used to characterize all three parameters for a single sample. This is shown in FIG. 13 where depth, abruptness and DF are mapped for a single sample wafer. The measurement methods may also be used as a part of a more complex analysis. This means, for example that there may be cases where these measurements methods will be used in combination with related measurements that analyze other USJ parameters (e.g., carrier mobility, etc.).

What is claimed is:

1. A method of evaluating the abruptness of a junction in a semiconductor sample, the method comprising:
   directing an intensity modulated pump beam and a probe beam on the sample surface;
   obtaining two or more measurements by analyzing the reflected probe beam, each measurement composed of an in-phase (I) value and a quadrature (Q) value where at least one measurement is obtained after changing the relative position of the pump and probe beams on the sample surface;
   deriving the slope of a line in the I-Q plane fitted to the I and Q values that compose the measurements;
   comparing the derived slope with previously derived slopes associated with calibration samples having a known junction abruptness to derive an abruptness value for the measured sample; and
   storing the derived abruptness value.

2. A method as recited in claim 1, wherein one of the measurements is obtained when the pump and probe beams are overlapping.

3. A method as recited in claim 1, where the I and Q values are compared to I and Q values obtained from one or more calibration samples having known junction abruptness values.

4. A method as recited in claim 1, wherein said decay factor is calculated by dividing the results of the second measurement by the results of the first measurement.

5. A method of evaluating the abruptness of a junction in a semiconductor sample comprising:
   directing an intensity modulated pump beam to a spot on the sample to periodically excite a region of the sample;
   directing a probe beam to a first measurement spot within the periodically excited region of the sample;
   monitoring the reflected probe beam and generating first output signals;

directing the probe beam to a second measurement spot within the periodically excited region of the sample, said second measurement spot being spaced from the first measurement spot;

monitoring the reflected probe beam and generating second output signals;

filtering and processing the output signals to create in-phase (I) and quadrature (Q) components and analyzing the I and Q components derived from the two different measurement spots to determine the abruptness of the junction, wherein the processing includes analyzing the slope of a line fit to the I and Q components derived from the measurement points as plotted in I and Q space; and storing the determined abruptness of the junction.

6. A method as recited in claim 5, wherein one of the measurement spots is coincident with the pump beam spot.

7. A method of evaluating the abruptness of a junction in a semiconductor sample, the method comprising:

focusing an intensity modulated pump beam and a probe beam on the sample surface;

obtaining two or more measurements by analyzing the reflected probe beam, each measurement composed of an in-phase (I) value and a quadrature (Q) value where each at least one measurement is obtained after changing the power density of the pump beam on the sample surface;

deriving the slope of a line in the I-Q plane fitted to the I and Q values that compose the measurements;

comparing the derived slope with previously derived slopes associated with calibration samples having a known junction abruptness to derive an abruptness value for the measured sample; and storing the derived abruptness value.

8. A method as recited in claim 7, wherein the power density of the pump beam is changed by changing the spot size of the pump beam on the sample.

9. A method as recited in claim 7, wherein the power density of the pump beam is changed passing the pump beam through a filter.

10. A method of evaluating the abruptness of a junction in a semiconductor sample comprising:

directing an intensity modulated pump beam to a spot on the sample to periodically excite a region of the sample;

directing a probe beam to a measurement spot within the periodically excited region of the sample;

monitoring the reflected probe beam and generating first output signals;

changing the power density of the pump beam;

monitoring the reflected probe beam and generating second output signals;

filtering and processing the output signals to create in-phase (I) and quadrature (Q) components and analyzing the I and Q components derived from the two different power densities to determine the abruptness of the junction wherein the processing includes analyzing the shape of a line fit to the I and Q components derived from the measurement points as plotted in I and Q space; and storing the determined abruptness of the junction.

11. A method as recited in claim 10, wherein the power density of the pump beam is changed by changing the cross-sectional size of the pump beam.

12. A method as recited in claim 10, wherein the power density of the pump beam is changed passing the pump beam through a filter.

13. A method of characterizing a semiconductor sample, the method comprising:

directing an intensity modulated pump beam and a probe beam on the sample surface;

obtaining two or more measurements by analyzing the reflected probe beam, where one measurement follows the previous measurements after a predetermined period of time;

fitting the measurements to a curve by using a function with two or more variables; and characterizing the incompleteness of an annealing process and/or the presence of surface states by evaluating the curve; and storing the characterized incompleteness of the annealing process and/or the presence of surface states.

14. A method as recited in claim 13, in which a change in the function is calculated as the value of the curve sampled at an initial time divided by the value of the curve sampled at a time corresponding to the predetermined time period.

15. A method of evaluating two or more properties of a junction formed in a semiconductor sample, the method comprising:

directing an intensity-modulated pump beam and a non-modulated probe beam on the surface of a sample;

determining the in-phase (I) and quadrature (Q) components of the reflected probe beam intensity;

deriving the slope of a line in the I-Q plane fitted to the determined I and Q components;

using the derived slope in combination with a previously derived slope associated with a calibration sample having a known junction abruptness to derive two or more properties of the junction; and storing the derived properties of the junction.

16. A method of evaluating the incompleteness of an annealing process and/or the presence of surface states of a semiconductor sample, the method comprising:

directing an intensity modulated pump beam to the surface of the sample to periodically excite a region on the sample;

directing a probe beam to a spot within the periodically excited region;

obtaining a first measurement of the modulated changes in the reflected intensity of the probe beam induced by the periodic excitation;

continuing to periodically excite the sample for a predetermined time period;

obtaining a second measurement of the modulated changes in the reflected intensity of the probe beam induced by the periodic excitation;

calculating a decay factor based on the first and second measurements;

using the decay factor to evaluate the incompleteness of an annealing process and/or the presence of surface states of a semiconductor sample; and storing the evaluated incompleteness of the annealing process and/or the presence of surface states.

* * * * *